(12) United States Patent
Hawkins et al.

(10) Patent No.: US 8,087,707 B1
(45) Date of Patent: Jan. 3, 2012

(54) MULTIFUNCTION DEVICE FOR PEOPLE WITH LIMITED MOBILITY

(76) Inventors: Bryan J. Hawkins, Tulsa, OK (US);
Steve Swisher, Broken Arrow, OK (US)

( * ) Notice: Subject to any disclaimer, the term of this patent is extended or adjusted under 35 U.S.C. 154(b) by 0 days.

(21) Appl. No.: 12/958,814

(22) Filed: Dec. 2, 2010

(51) Int. Cl.
*A47F 13/06* (2006.01)

(52) U.S. Cl. .......................................... 294/24; 223/111

(58) Field of Classification Search .................. 294/24, 294/211; 223/111–113; 135/66, 77, 80, 135/65, 68
See application file for complete search history.

(56) References Cited

U.S. PATENT DOCUMENTS

| | | | |
|---|---|---|---|
| 1,116,797 A | 11/1914 | Carmichael et al. | |
| 3,179,436 A * | 4/1965 | Choy | 280/812 |
| 3,591,226 A | 7/1971 | Elmore | |
| 4,374,600 A | 2/1983 | Van Zelm | |
| 4,613,179 A | 9/1986 | Van Zelm | |
| 4,709,839 A | 12/1987 | Tucker | |
| 4,758,035 A | 7/1988 | Shimasaki | |
| 4,790,339 A | 12/1988 | Bennett | |
| 5,065,917 A * | 11/1991 | Diehm | 223/113 |
| 5,249,720 A | 10/1993 | White | |
| 5,370,432 A | 12/1994 | Kram | |
| 5,687,889 A | 11/1997 | Liden | |
| 5,865,203 A * | 2/1999 | Villano | 135/65 |
| 6,446,848 B1 * | 9/2002 | Swisher | 223/112 |
| 6,669,254 B2 | 12/2003 | Thom et al. | |
| 2006/0025290 A1 | 2/2006 | House | |

* cited by examiner

*Primary Examiner* — Saul Rodriguez
*Assistant Examiner* — Gabriela Puig
(74) *Attorney, Agent, or Firm* — Head, Johnson & Kachigian, P.C.

(57) ABSTRACT

A multifunction device for people with limited mobility allows a person to perform a variety of everyday activities with greater ease using a single device. The device has a gripper, which may be used as a shoehorn or to pick up small items; a leg lift, which may be used to reduce stress on the hip and/or knee when making leg movements; and a finger assembly, which may be used to push or pull light objects such as bedding and clothing.

10 Claims, 3 Drawing Sheets

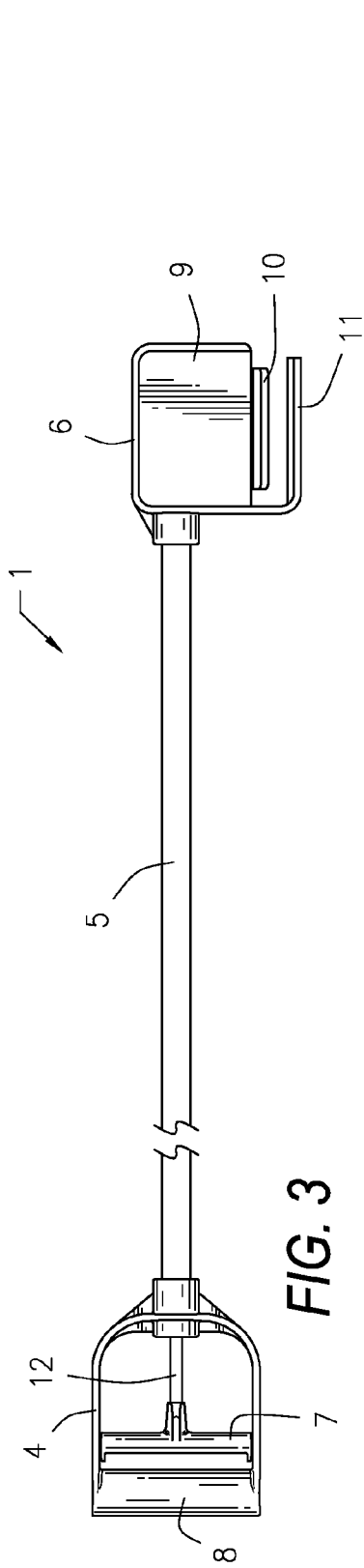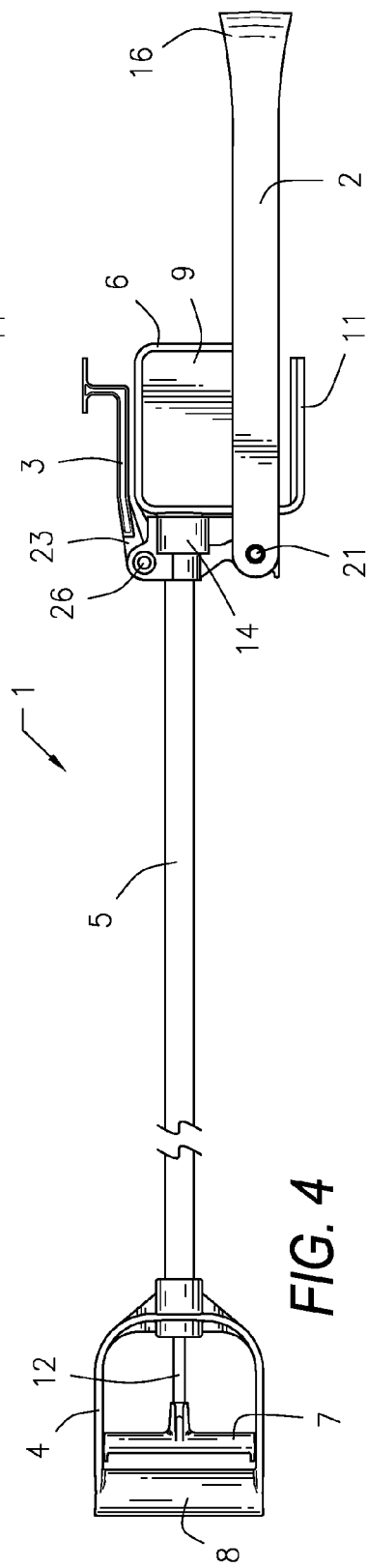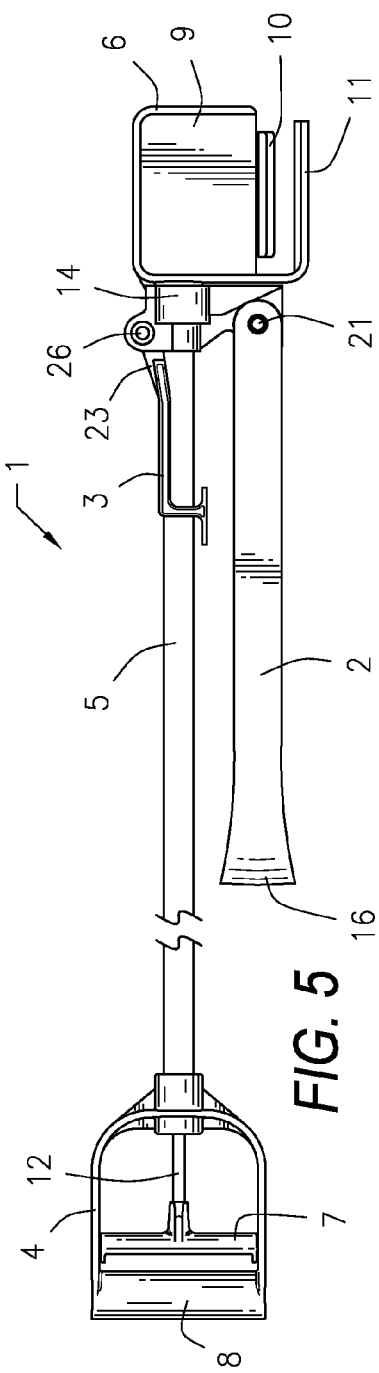

MULTIFUNCTION DEVICE FOR PEOPLE WITH LIMITED MOBILITY

BACKGROUND OF THE INVENTION

1. Field of the Invention

This invention relates generally to a device to be used by a person with limited mobility to assist with daily activities, and more particularly to a single device that perform multiple functions, such as acting as a leg lift, a shoe horn, a gripper, a sock remover, and a dressing aid.

2. Description of the Related Art

Typically, after hip or knee surgery, a patient purchases a kit with tools to make the performance of everyday tasks easier during recovery. Such a kit may include anywhere from four to eight different items. Available kits often contain low quality items, making it look as if the patient is getting more from them than they really receive. The tools in the kits are often difficult to use, and are all separate, forcing the patient to keep up with the various elements. Despite the variety of tools available in current kits, not a single kit offers one of the most essential items for recovery: a leg lift.

It is therefore desirable to provide a single device that incorporates the functions of the various elements typically included in a hip or knee kit. It is further desirable for the single device to incorporate a leg lift. It is further desirable for the device to be a single, compact, easy to use device.

SUMMARY OF THE INVENTION

In general, the invention relates to a device comprising a grasper assembly, a mount, a leg lift stirrup assembly, and a finger assembly. The grasper assembly may comprise a shaft with a first end and a second end; a handle assembly attached to the first end of the shaft; and an engaging portion attached to the second end of the shaft, such that a user may grasp an object with the engaging portion while holding the handle assembly. The mount may be removably attached to the shaft of the grasper assembly. The leg lift stirrup assembly may be removably attached to the mount, and the leg lift stirrup assembly may comprise a stirrup such that the user with a foot may place the foot in the stirrup and lift the foot by pulling the handle assembly. The finger assembly may be removably attached to the mount, and the finger assembly may comprise fingers such that the user may engage an object with the fingers and push or pull the object by pushing or pulling the handle assembly.

The handle assembly may comprise a movable portion and a stationary portion, where the stationary portion is attached to and is stationary with respect to the shaft and where the movable portion is movable with respect to the stationary portion. The engaging portion may comprise a housing, a clamp, and a stop, and the stop may be connected to the movable portion of the handle assembly via a rod, where the rod extends through the shaft, such that squeezing the movable portion of the handle assembly toward the stationary portion of the handle assembly actuates the clamp such that the clamp moves toward and presses against the stop.

The mount is removably attached to the shaft adjacent the engaging portion. The mount may comprise a shaft snap ring, where the shaft snap ring may be snapped onto the shaft and fit snuggly thereon and may be removed from the shaft when desired; a finger housing slot; and a stirrup housing.

The leg lift stirrup assembly may further comprise a first mounting peg and a second mounting peg. The stirrup may have a first end and a second end, and the first mounting peg may be attached to the first end of the stirrup and the second mounting peg may be attached to the second end of the stirrup. The first mounting peg and the second mounting peg may fit together such that the stirrup forms a loop. The first mounting peg and the second mounting peg may fit within the stirrup housing. The first mounting peg and the second mounting peg may have a bore therethrough and a screw may be placed through the bore and held in place by a threaded insert such that the screw holds the stirrup in place relative to the shaft but allows the stirrup to pivot from an open position to a closed position. The stirrup assembly may be removable such that the stirrup may be removed from the device by removing the screw and the threaded insert from the first mounting peg and the second mounting peg and removing the first mounting peg and the second mounting peg from the stirrup housing.

The finger assembly may further comprises a mounting end with a bore therethrough, and the finger housing slot on the mount may comprise two sides with holes therein and a slot between the two sides, where the holes align with the bore when the mounting end of the finger assembly is placed within the slot. The finger assembly may further comprise a screw extending through the bore and the holes in the two sides of the finger housing slot, where the screw is held in place by a threaded insert, and where the screw holds the finger assembly in place relative to the shaft but allows the finger assembly to pivot from an open position to a closed position. The finger assembly may be removable such that the finger assembly may be removed from the device by removing the screw and the threaded insert from the bore and the two holes and removing the mounting end from the finger housing slot.

BRIEF DESCRIPTION OF THE DRAWINGS

FIG. 3 is a side view of the device with the finger and leg lift elements removed;

FIG. 4 is a side view of the device with the finger and leg lift elements in an open position;

FIG. 5 is a side view of the device with the finger and leg lift elements in a closed position;

Other advantages and features will be apparent from the following description, and from the claims.

DETAILED DESCRIPTION OF THE INVENTION

The devices discussed herein are merely illustrative of specific manners in which to make and use this invention and are not to be interpreted as limiting in scope.

While the devices have been described with a certain degree of particularity, it is to be noted that many modifications may be made in the construction and the arrangement of the structural and functional details disclosed herein without departing from the spirit and scope of this disclosure. It is understood that the devices are not limited to the embodiments set forth herein for purposes of exemplification.

Figure 1:
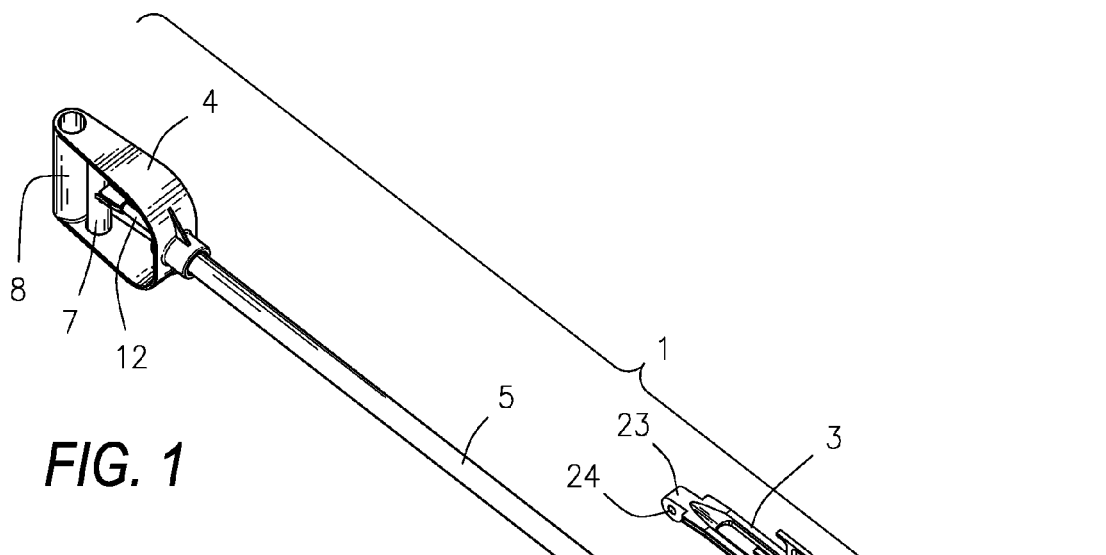
FIG. 1 is an exploded view of a multifunction device for people with limited mobility.

Referring to the figures of the drawings, wherein like numerals of reference designate like elements throughout the several views, and initially to FIG. 1, a multifunction device for use by people with limited mobility is provided. The device incorporates a shoehorn/grasper assembly 1, as set forth in U.S. Pat. No. 5,065,917 ("the '917 patent"), which is incorporated herein by reference; a leg lift stirrup assembly 2; and a finger assembly 3.

The shoehorn/grasper assembly 1 may comprise a handle assembly 4, a shaft 5, and an engaging portion 6. The handle assembly 4 may comprise a movable portion 7 and a stationary portion 8. The stationary portion 8 of the handle assembly 4 may be mounted on one end of the shaft 5, with the engaging portion 6 of the shoehorn/grasper assembly 1 mounted on the opposite end of the shaft 5. The engaging portion 6 may comprise a housing 9, a clamp 10, and a stop 11. The clamp 10 may be connected to the movable portion 7 of the handle assembly 4 via a rod 12, where the rod 12 extends through the shaft 5. Squeezing the movable portion 7 of the handle assembly 4 toward the stationary portion 8 of the handle assembly 4 may actuate the clamp 10 such that the clamp 10 moves toward and presses against the stop 11, as described in the '917 patent.

The shoehorn/grasper assembly 1 may be used for putting on socks or shoes without bending at the hip and/or leg. In use, the patient slides the stop 11 into the shoe or sock and actuates the clamp 10 toward the stop 11 by squeezing the movable portion 7 of the handle assembly 4 toward the stationary portion 8 of the handle assembly 4. The patient then inserts his or her foot into the shoe or sock, with the stop 11 acting as a shoe horn. Once the patient's foot is in place, the patient releases the movable portion 7 of the handle assembly 4, thus releasing the clamp 10 from the stop 11 and allowing removal of the shoehorn/grasper assembly 1 from the shoe or sock. The shoehorn/grasper assembly 1 may also be used for grasping items that are out of the patient's reach, allowing the patient to move such items without painful and possibly injurious movement. In use, the patient places shoehorn/grasper assembly 1 such that the stop 11 is on one side of the object to be moved and the clamp 10 is on the other. The patient actuates the clamp 10 toward the stop 11 by squeezing the movable portion 7 of the handle assembly 4 toward the stationary portion 8 of the handle assembly 4 to grasp the object, and releases the movable portion 7 of the handle assembly 4 to release the object.

Figure 2:
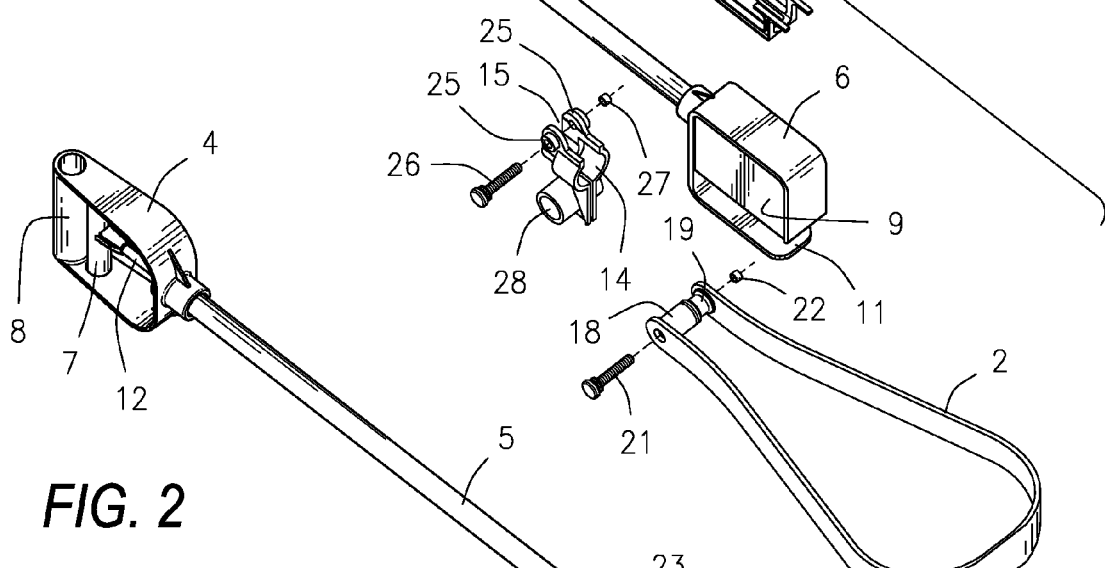
FIG. 2 a perspective view of the device.

The leg lift stirrup assembly 2 and the finger assembly 3 may attach to the shaft 5 of the shoehorn/grasper assembly via a mount 13. The mount may comprise a shaft snap ring 14, which may be snapped onto the shaft 5 and fit snuggly thereon; a finger housing slot 15; and a stirrup housing 28. The leg lift stirrup assembly 2 may comprise a stirrup 16 and mounting pegs 18 and 19, each attached to one end of the stirrup 16. The leg lift stirrup assembly 2 may further comprise two tension washers 31 and 32. The mounting pegs 18 and 19 may fit together such that the stirrup 16 forms a loop. The mounting pegs 18 and 19 may fit within the stirrup housing 28. The mounting pegs 18 and 19 may have a bore 20 therethrough such that a screw 21 may fit through the bore 20 and be held in place by a threaded insert 22. Thus, the mounting pegs 18 and 19 may be placed within the stirrup housing 28, the screw 21 may be placed through the bore 20 in the mounting pegs 18 and 19, and the screw 21 may be tightened into the threaded insert 22 such that the stirrup 16 is held in place relative to the shaft 5, but is capable of being rotated from an open position, as shown in FIGS. 2 and 4, and a closed position, as shown in FIG. 5.

The stirrup 16 may be used as a leg lift. Such use reduces stress on the hip and/or knee when making leg movements. The patient may use a combination of leg strength and stirrup pulling pressure to move his or her leg. In use, the patient slides the stirrup 16 over the end of his or her foot. The patient positions the stirrup so that it is securely in the arch of the foot and locks his or her knee in place. The patient grabs the handle 8 and pulls gently until the stirrup 16 is tight against the bottom of the foot. While maintaining constant and consistent pulling pressure on the stirrup 16, the patient gently lifts his or her leg into the desired position. The patient then carefully removes the stirrup 16 from his or her foot.

As the patient recovers, he or she may no longer desire to use the stirrup 16. The leg lift stirrup assembly 2 may then be removed from the mount 13 by removing the screw 21 and removing the mounting pegs 18 and 19 from the stirrup housing 28.

Figure 6:
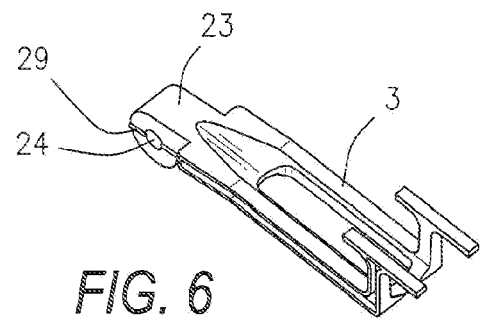
FIG. 6 is a perspective view of the finger element.
Figure 7:
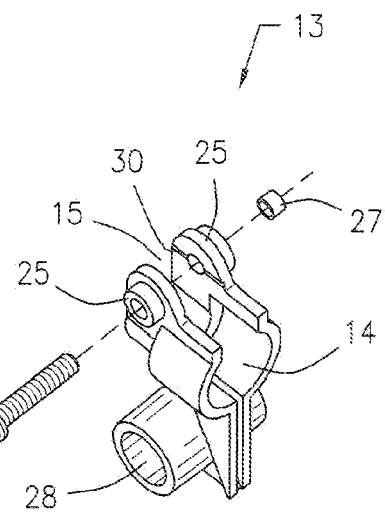
FIG. 7 is an exploded view of the mount for the finger and leg lift elements.
Figure 8:
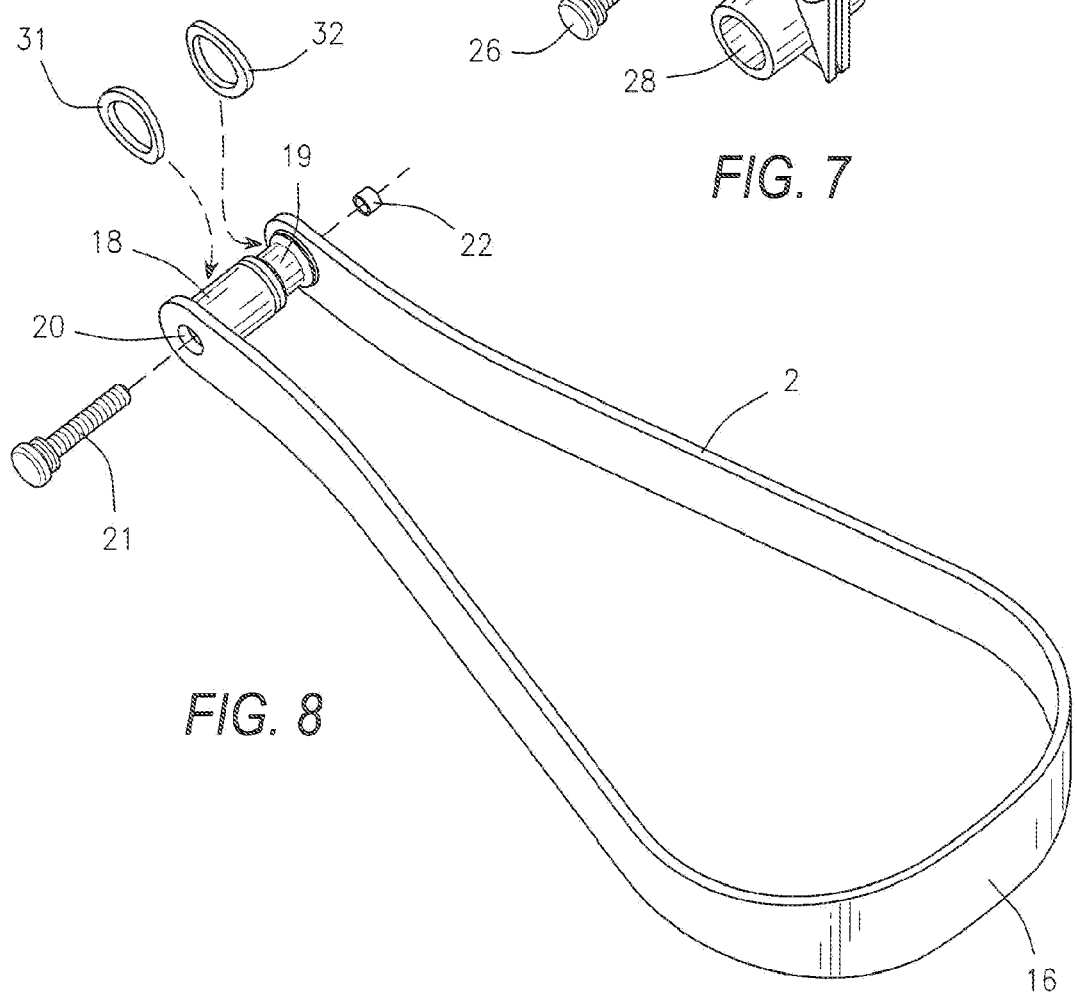
FIG. 8 is an exploded view of the leg lift element.

The finger assembly 3 may have a mounting end 23 with a bore 24 therethrough. The mounting end 23 may fit into the finger housing slot 15 in the mount 13. The finger mounting slot 15 may have holes 25 on either side thereof. A screw 26 may be placed through the holes 25 and the bore 24 and may be secured into a threaded insert 27 such that the finger assembly 3 is held in place relative to the shaft 5, but is capable of being rotated from an open position, as shown in FIGS. 2 and 4, and a closed position, as shown in FIG. 5. The mounting end 23 may have ribs 29 on its sides such that the ribs 29 may fit within grooves 30 in the sides of the finger housing slot 15 in the mount 13 to lock the finger assembly 3 into place. One side of the ribs 29 may be seen in FIG. 6 and one side of the grooves 30 may be seen in FIG. 7.

The finger assembly 3 may be used to push and pull light objects, such as bedding and clothing. In use, the patient locks the finger assembly 3 into place on top of the grasper housing 9 and aligns the fingers assembly 3 with the desired object. Holding the handle 8, the patient pulls or pushes the object to move it into the desired position.

As the patient recovers, he or she may no longer desire to use the finger assembly 3. The finger assembly 3 may then be removed from the mount 13 by removing the screw 26 and removing the mounting end 23 from the finger housing slot 15. If the stirrup is likewise no longer in use, the entire mount 13 may be removed from the shaft 5 and the shoehorn/grasper assembly 1 may be used alone.

The multifunction device may be used by people with short term needs, such as patients recovering from surgery or injury, or by people with long term needs, such as patients suffering from stroke, neurological injury, or chronic pain. The device replaces the typical bag of tools with a single, compact, easy to use device. The device functions as a leg lift, shoe horn, gripper, sock remover, and dressing aid. The single device saves patients from the time and hassle of trying to find needed recovery items, and gives patients the items they need for their daily living activities. The device combines many of the items a patient needs into one product for ease of use.

Whereas, the devices have been described in relation to the drawings and claims, it should be understood that other and further modifications, apart from those shown or suggested herein, may be made within the spirit and scope of this invention.

What is claimed is:
1. A device comprising:
   a grasper assembly comprising:
     a shaft with a first end and a second end;
     a handle assembly attached to the first end of the shaft; and
     an engaging portion attached to the second end of the shaft;
     such that a user may grasp an object with the engaging portion while holding the handle assembly;
   a mount removably attached to the shaft of the grasper assembly;

a leg lift stirrup assembly removably attached to the mount, the leg lift stirrup assembly comprising a stirrup such that the user with a foot may place the foot in the stirrup and lift the foot by pulling the handle assembly; and a finger assembly removably attached to the mount, the finger assembly comprising fingers such that the user may engage an object with the fingers and push or pull the object by pushing or pulling the handle assembly.

2. The device of claim 1 where:

the handle assembly comprises a movable portion and a stationary portion, where the stationary portion is attached to and is stationary with respect to the shaft and where the movable portion is movable with respect to the stationary portion;

the engaging portion comprises a housing, a clamp, and a stop; and the clamp is connected to the movable portion of the handle assembly via a rod, where the rod extends through the shaft, such that squeezing the movable portion of the handle assembly toward the stationary portion of the handle assembly actuates the clamp such that the clamp moves toward and presses against the stop.

3. The device of claim 1 where the mount is removably attached to the shaft adjacent the engaging portion.

4. The device of claim 1 where the mount comprises:

a shaft snap ring, where the shaft snap ring may be snapped onto the shaft and fit snuggly thereon and may be removed from the shaft when desired;

a finger housing slot; and a stirrup housing.

5. The device of claim 4 where:

the leg lift stirrup assembly further comprises a first mounting peg and a second mounting peg;

the stirrup has a first end and a second end;

the first mounting peg is attached to the first end of the stirrup and the second mounting peg is attached to the second end of the stirrup;

the first mounting peg and the second mounting peg fit together such that the stirrup forms a loop; and the first mounting peg and the second mounting peg fit within the stirrup housing.

6. The device of claim 5 where the first mounting peg and the second mounting peg have a bore therethrough and a screw may be placed through the bore and held in place by a threaded insert such that the screw holds the stirrup in place relative to the shaft but allows the stirrup to pivot from an open position to a closed position.

7. The device of claim 6 where the stirrup assembly is removable such that the stirrup may be removed from the device by removing the screw and the threaded insert from the first mounting peg and the second mounting peg and removing the first mounting peg and the second mounting peg from the stirrup housing.

8. The device of claim 4 where:

the finger assembly further comprises a mounting end with a bore therethrough; and the finger housing slot on the mount comprises two sides with holes therein and a slot between the two sides, where the holes align with the bore when the mounting end of the finger assembly is placed within the slot.

9. The device of claim 8 where the finger assembly further comprises a screw extending through the bore and the holes in the two sides of the finger housing slot, where the screw is held in place by a threaded insert, and where the screw holds the finger assembly in place relative to the shaft but allows the finger assembly to pivot from an open position to a closed position.

10. The device of claim 9 where the finger assembly is removable such that the finger assembly may be removed from the device by removing the screw and the threaded insert from the bore and the two holes and removing the mounting end from the finger housing slot.

* * * * *